US005753699A

United States Patent [19]
Greff et al.

[11] Patent Number: 5,753,699
[45] Date of Patent: May 19, 1998

[54] METHODS FOR TREATING NON-SUTURABLE, SUPERFICIAL WOUNDS BY USE OF CYANOACRYLATE ESTER COMPOSITIONS COMPRISING AN ANTIMICROBIAL AGENT

[75] Inventors: Richard J. Greff, St. Pete Beach, Fla.; Michael M. Byram, Colorado Springs, Colo.

[73] Assignee: MedLogic Global Corporation, Colorado Springs, Colo.

[21] Appl. No.: 947,792

[22] Filed: Oct. 9, 1997

Related U.S. Application Data

[63] Continuation-in-part of Ser. No. 781,409, Jan. 10, 1997, Pat. No. 5,684,042.

[51] Int. Cl.[6] .............. A61K 31/255; C07C 255/10
[52] U.S. Cl. .............................. 514/527; 558/443
[58] Field of Search ...................... 514/527; 558/443

[56] References Cited

U.S. PATENT DOCUMENTS

| | | | |
|---|---|---|---|
| 2,706,701 | 4/1955 | Beller et al. | 167/70 |
| 2,784,127 | 3/1957 | Joyner et al. | 154/43 |
| 2,826,532 | 3/1958 | Hosmer | 167/70 |
| 2,900,305 | 8/1958 | Siggin | 167/70 |
| 4,374,126 | 2/1983 | Cardarelli et al. | 424/81 |
| 4,444,933 | 4/1984 | Columbus et al. | 524/292 |
| 4,542,012 | 9/1985 | Dell | 424/28 |
| 4,713,235 | 12/1987 | Krall | 424/5 |
| 4,978,527 | 12/1990 | Brink et al. | 424/78 |
| 4,994,542 | 2/1991 | Matsuda et al. | 528/70 |
| 5,051,256 | 9/1991 | Barnes | 424/702 |
| 5,069,907 | 12/1991 | Mixon et al. | 424/445 |
| 5,254,132 | 10/1993 | Barley et al. | 606/214 |
| 5,328,687 | 7/1994 | Leung et al. | 424/78.35 |
| 5,480,935 | 1/1996 | Greff et al. | 524/776 |
| 5,547,662 | 8/1996 | Khan et al. | 424/78.03 |
| 5,665,817 | 9/1997 | Greff et al. | 524/776 |
| 5,684,042 | 11/1997 | Greff et al. | 514/527 |

FOREIGN PATENT DOCUMENTS

WO 93/25196  12/1993  WIPO.
WO 96/23532   8/1996  WIPO.

OTHER PUBLICATIONS

Ritter, M.A., et al., "Retrospective Evaluation of an iodophor–Incorporated Antimicrobial Plastic Adhesive Wound Drape"—Clinical Orthopedics and Related Research, (1986) pp. 307–308.

Sidorova, et al., Preventing Incompetence of Uterine Sutures after Ceasarian Section, Akusherstvo I. Ginekologiia, (Mar. 1989) 3:30–33 (Abstract Only).

Primary Examiner—Johann Richter
Assistant Examiner—Ebenezer Sackey
Attorney, Agent, or Firm—Burns, Doane, Swecker & Mathis, L.L.P.

[57] ABSTRACT

Antimicrobial cyanoacrylate compositions are applied to non-suturable, superficial wound surfaces. In situ polymerization of the cyanoacrylate ester provides for a polymeric film over the wound which promotes wound healing and retards infection of the wound.

10 Claims, No Drawings

METHODS FOR TREATING NON-SUTURABLE, SUPERFICIAL WOUNDS BY USE OF CYANOACRYLATE ESTER COMPOSITIONS COMPRISING AN ANTIMICROBIAL AGENT

CROSS-REFERENCE TO RELATED APPLICATIONS

This application is a continuation-in-part of application Ser. No. 08/781,409 now U.S. Pat. No. 5,684,042 filed Jan. 10, 1997 and entitled "Cyanoacrylate Compositions Comprising an Antimicrobial Agent" which application is incorporated herein by reference in its entirety.

BACKGROUND OF THE INVENTION

FIELD OF THE INVENTION

This invention is directed to methods for treating non-suturable superficial wounds by using polymerizable cyanoacrylate compositions comprising a compatible antimicrobial agent and, in particular, an iodine containing antimicrobial agent. These antimicrobial cyanoacrylate compositions provide for in situ formation of an antimicrobial polymeric cyanoacrylate film covering the wound.

REFERENCES

The following publications, patent applications and patents are cited in this application as superscript numbers:

1. Barley, et al., International Patent Application Publication No. WO 93/25196, for *Methods for Treating Non-Suturable Wounds by Use of Cyanoacrylate Adhesives*, published Dec. 23, 1993
2. Barley, et al., *Methods for Treating Suturable Wounds by Use of Sutures and Cyanoacrylate Adhesives*, U.S. Pat. No. 5,254,132, issued Oct. 19, 1993
3. Greff, et al., U.S. Pat. No. 5,480,935, *Cyanoacrylate Adhesive Compositions*, issued Jan. 2, 1996
4. Beller, et al., *Process for the Preparation of Iodine-Polyvinylpyrrolidone by Dry Mixing*, U.S. Pat. No. 2,706,701, issued Apr. 19, 1955
5. Hosmer, *Process of Stabilizing Polyvinylpyrrolidone*, U.S. Pat. No. 2,826,532, issued Mar. 11, 1958
6. Siggin, *Preparation of Iodine Polyvinylpyrrolidone Adducts*, U.S. Pat. No. 2,900,305, issued Aug. 18, 1958
7. Joyner, et al., *Plasticized Monomeric Adhesive Compositions and Articles Prepared Therefrom*, U.S. Pat. No. 2,784,127, issued Mar. 5, 1957
8. Columbus, et al., *Adhesive Cyanoacrylate Compositions with Reduced Adhesion to Skin*, U.S. Pat. No. 4,444,933, issued Apr. 24, 1984
9. Leung, et al., *Biocompatible Monomer and Polymer Compositions*, U.S. Pat. No. 5,328,687, issued Jul. 12, 1994
10. Leplyanin, "*Medical and Surgical Adhesive Composition and Process for Its Preparation*", International Application Publication No. WO 96/23532 published Aug. 8, 1996
11. Greff, et al., *Cyanoacrylate Adhesive Compositions*, U.S. Pat. No. 5,665,817, issued Sep. 9, 1997

All of the above patent applications and patents are herein incorporated by reference in their entirety to the same extent as if each individual publication, patent application or patent was specifically and individually indicated to be incorporated by reference in its entirety.

STATE OF THE ART

Polymerizable cyanoacrylate esters have been disclosed for a variety topical uses on mammalian skin including use in covering small non-suturable superficial wounds on skin surfaces[1] as well as in closing suturable wounds.[2] Polymerizable cyanoacrylate esters suggested for such uses include cyanoacrylate esters of formula I:

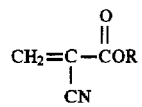

wherein R is an alkyl or other suitable substituent. Such cyanoacrylate esters are disclosed in U.S. Pat. Nos. 3,527,224; 3,591,676; 3,667,472; 3,995,641; 4,035,334; and 4,650,826. Preferably, when applied to mammalian tissue, R is an alkyl group of from 1 to 10 carbon atoms and most often is butyl or octyl (e.g., n-butyl or n-octyl). These compositions are liquid in nature and, upon contact with surface skin proteins and moisture, will polymerize to provide a solid film over the skin surface.

Cyanoacrylate ester compositions for topical skin application typically are formulated to contain both a plasticizer to enhance flexibility of the resulting polymeric film and a polymerization inhibitor to avoid premature polymerization of the formulation. When employed topically on mammalian skin, Greff et al.[3,11] disclose that the cyanoacrylate ester composition preferably employs from about 50 to about 500 ppm sulfur dioxide as the polymerization inhibitor and from about 18–25 weight percent of a biocompatible plasticizer such as dioctyl phthalate or acetyl tri-n-butyl citrate.

Notwithstanding the benefits associated with the use of polymerizable cyanoacrylate ester compositions for application over small non-suturable superficial wounds, these compositions do not have a broad spectrum of antimicrobial activitiy including activity against microbial spores and, accordingly, cannot guarantee reductions in microbial populations on mammalian skin surface either under or adjacent the polymeric cyanoacrylate film formed in situ on the skin. Accordingly, the use of polymerizable cyanoacrylate ester compositions for treating small non-suturable superficial wounds as described by Barley, et al.[1] would be significantly augmented if these compositions were also antimicrobial.

Because polymerizable cyanoacrylate ester compositions are not sufficiently antimicrobial by themselves, incorporation of broad antimicrobial properties into the cyanoacrylate polymeric film necessitates, of course, that an antimicrobially effective amount of an antimicrobial agent be incorporated into the polymerizable cyanoacrylate ester composition and that sufficient amounts of this agent be released from the resulting polymeric cyanoacrylate film formed in situ on the patient's skin such that an antimicrobial effect is achieved. The incorporation of such an antimicrobial agent into the cyanoacrylate ester composition is problematic at best because several disparate criteria must be simultaneously met. First, the antimicrobial agent must be soluble or dispersible in the cyanoacrylate ester composition at the concentrations necessary to effect antimicrobial properties. Second, the antimicrobial agent employed must not cause premature polymerization of the cyanoacrylate ester composition. Third, the antimicrobial agent employed must not prevent in situ polymerization of the cyanoacrylate ester composition when applied to the skin. Fourth, the antimicrobial agent must be compatible with the intended use of the polymeric film by not inhibiting formation of a flexible, durable film. Fifth, the impregnated antimicrobial agent must be released from the polymerized film in situ on the patient's skin in sufficient amounts to be antimicrobial.

Because of these disparate properties, many conventional antimicrobial agents are unsuitable for use in the polymerizable cyanoacrylate ester compositions used in the methods of this invention. However, in view of the clear benefits associated with the incorporation of an antimicrobial agent directly into these compositions, methods for treating small, non-suturable superficial wounds using an antimicrobial cyanoacrylate ester compositions would be particularly beneficial.

SUMMARY OF THE INVENTION

This invention is drawn to methods for treating and/or protecting non-suturable superficial or small wounds by the application of an antimicrobial polymerizable cyanoacrylate ester composition to the surface of such wounds providing for the in situ formation of an antimicrobial polymeric cyanoacrylate film on mammalian skin over the treated wound.

In particular, this invention is directed to methods for treating non-suturable superficial or small wounds which methods utilize cyanoacrylate ester compositions comprising an antimicrobially effective amount of a compatible iodine containing antimicrobial agent. These compositions provide for in situ formation of an antimicrobial polymeric cyanoacrylate film on mammalian skin over the treated wound. The specific antimicrobial agent employed is compatible with the cyanoacrylate ester composition insofar as the antimicrobial agent neither causes premature polymerization nor prevents polymerization of the monomer or reactive oligomer, rather a flexible and durable polymer film is formed in situ on mammalian skin by this composition. Moreover, in vitro assays evidence that the antimicrobial agent is released from the polymeric film in antimicrobially effective amounts thereby imparting antimicrobial properties to the polymeric film formed in situ over the wound.

The compatible iodine containing antimicrobial agent comprises an antimicrobial complex of iodine molecules with a biocompatible polymer. Suitable biocompatible polymers include, by way of example only, polyvinylpyrrolidinone polymers which is also referred to under the common name of Povidone or PVP. PVP polymers form complexes with iodine which are antimicrobial in nature and are available commercially as Povidone-Iodine.

This invention is based, in part, on the discovery that application of an antimicrobial polymerizable cyanoacrylate ester composition to a non-suturable superficial or small wound provides for an antimicrobial polymeric film over the wound which ensures that not only is this wound protected by the polymeric film from exogenous materials but also the likelihood of infection in the wound is reduced.

The methods of this invention involve applying an antimicrobial cyanoacrylate ester composition onto a non-suturable superficial wound and allowing the composition to polymerize to form an antimicrobial polymeric film over the wound.

In the case of cuts, the antimicrobial cyanoacrylate ester composition is preferably applied to the separated skin defining the cut as well as over the cut, preferably when the skin sections are brought into apposition. The antimicrobial cyanoacrylate ester composition is then allowed to polymerize so as to both bind the separated skin sections and form an antimicrobial polymeric film over the cut. In addition to serving as a protective layer, the polymeric film also serves to promote healing and to retard infection of the cut.

In the case of abrasions, the antimicrobial cyanoacrylate ester composition is generally applied over the abrasion. The antimicrobial cyanoacrylate ester composition is allowed to polymerize so as to form an antimicrobial polymeric film over the abrasion. The polymer film serves to act as a protective layer which prevents further aggravation to the abrasion while also promoting healing and retarding infection of the abrasion.

Accordingly, in one of its method aspects, this invention is directed to a method for treating and/or protecting non-suturable superficial wounds which comprises:

applying to the surface of a non-suturable superficial wound a sufficient amount of an antimicrobial polymerizable cyanoacrylate ester composition so as to cover the entire wound area wherein the superficial wound is characterized as a superficial cut and/or abrasion which does not penetrate through the dermal layer of the skin surface to the subcutaneous layer; and polymerizing the antimicrobial cyanoacrylate ester composition so as to join separated skin sections and/or to form an antimicrobial polymeric film which adheres to the area where the composition was applied, wherein the antimicrobial cyanoacrylate ester composition comprises:

(a) a polymerizable cyanoacrylate ester; and
(b) an antimicrobially effective amount of a complex of iodine molecules with a biocompatible polymer.

Preferably, the polymerizable cyanoacrylate ester is a polymerizable monomer or reactive oligomer of a cyanoacrylate ester which, in monomeric form, is represented by formula I:

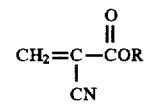

wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

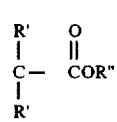

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula I, R is alkyl of from 2 to 10 carbon atoms and still more preferably alkyl of from 4 to 10 carbon atoms. Even more preferably, R is butyl, octyl, decyl or mixtures thereof. Most preferably, R is n-butyl so that the cyanoacrylate ester in monomeric form, is represented by formula II:

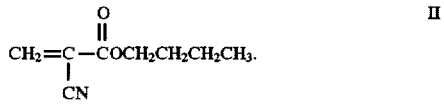

Preferred complexes of iodine molecules with a biocompatible polymer include povidone-iodine (commercially available from BASF, Mt. Olive, N.J., U.S.A).

DETAILED DESCRIPTION OF THE PREFERRED EMBODIMENTS

This invention is directed to methods for treating and/or protecting non-suturable superficial wound surfaces with polymerizable cyanoacrylate ester compositions comprising an antimicrobially effective amount of a compatible iodine containing antimicrobial agent. However, prior to discussing this invention in further detail, the following terms will first be defined.

Definitions

As used herein, the following terms have the following meanings:

The term "non-suturable superificial or small wounds" means superficial cuts and abrasions which do not penetrate through the dermal layer of the skin surface to the subcutaneous layer. Such superficial wounds include cuts where the skin is separated and can be joined together, as well as abrasions such as "nicks" or "scrapes" where the skin is removed. Non-suturable wounds do not, however, include puncture wounds. Such non-suturable superficial or small wounds are sometimes referred to herein as "non-suturable superficial wounds".

In view of the above, non-suturable superficial wounds as defined herein include common cuts and scratches which rarely need medical attention unless located in a sensitive area or unless infection occurs at the wound site. As opposed to the edges of suturable wounds which can be widely separated, the edges of non-suturable superficial wounds can easily be opposed or brought together. Examples of non-suturable superficial wounds treatable by the methods of this invention include skin tearing adjacent the site of a catheter, superficial skin wounds resulting from everyday cuts and abrasions.

The term "polymerizable cyanoacrylate esters compositions" refers to polymerizable compositions comprising cyanoacrylate ester monomers and/or polymerizable oligomers which, in their monomeric form, are preferably compounds represented by formula I as described above.

More preferably, in formula I, R is an alkyl group of from 1 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, octyl, decyl or mixtures thereof and most preferably, R is n-butyl. Mixtures of such compounds can also be employed. These polymerizable cyanoacrylate esters are known in the art and are described in, for example, U.S. Pat. Nos. 3,527,224; 3,591,676; 3,667, 472; 3,995,641; 4,035,334; and 4,650,826 the disclosures of each are incorporated herein by reference in their entirety.

The polymerizable cyanoacrylate esters described herein rapidly polymerize in the presence of water vapor or tissue protein, and the n-butyl-cyanoacrylate bonds human skin tissue without causing histotoxicity or cytotoxicity.

The term "a biocompatible polymer" refers to polymers which, as iodine complexes (adducts), are compatible with in vivo applications of cyanoacrylate ester compositions onto mammalian skin including human skin. Representative polymers include polyvinylpyrrolidone, copolymers comprising polyvinylpyrrolidone which is optionally crosslinked, and the like. Suitable copolymers include copolymers of polyvinylpyrrolidone and vinyl acetate or other vinyl compounds which copolymers are optionally crosslinked with a polyisocyanate. The molecular weight of these polymers is not critical with number average molecular weights ranging from about 10,000 to about 1,000,000 and preferably from 30,000 to 300,000 being preferred.

The term "a complex of iodine molecules with a biocompatible polymer" refers to an antimicrobial complex formed by the addition of iodine ($I_2$) to the biocompatible polymer. Such complexes are well known in the art and the resulting complex typically comprises both available iodine and iodine anions. These complexes, on contact with mammalian skin, are antimicrobial apparently by providing for a source of antimicrobial iodine. In any event, such complexes are employed only as starting materials herein and, by themselves, do not form a part of this invention.

These complexes are sometimes referred to herein simply by the term "iodine/polymer complexes". Such iodine/polymer complexes are distinguished from antibiotics which are frequently naturally derived materials from either bacteria or fungi and whose mode of action is to interfere with bacterial processes resulting in bacterial death. Contrarily, the complexes used in this invention are indiscriminate in destroying any microbes including fungi, viruses and bacteria apparently by release of iodine into the microbes and, accordingly, are properly referred to as antimicrobial agents. Surprising, it has been found that of the antimicrobial agents tested, only the iodine/polymer complexes are compatible in cyanoacrylate ester compositions. In fact, elemental (solid) iodine is incompatible with cyanoacrylate ester compositions because the addition of elemental iodine renders such compositions non-polymerizable on mammalian skin. Accordingly, complexation of the iodine with the biocompatible polymer is apparently essential for compatibility with the cyanoacrylate ester composition.

A preferred iodine/polymer complex for use in the compositions of this invention is a polyvinylpyrrolidone iodine complex which is described in, for example, U.S. Pat. Nos. 2,706,701, 2,826,532 and 2,900,305[4,5,6] as well as at pp. 1220 of the Eleventh Edition of the Merck Index, Published by Merck & Co., Rahway, N.J., USA (1989) the disclosures of which are incorporated herein by reference in their entirety. This complex is commercially available under the name "povidone-iodine" from BASF, Mt. Olive, N.J., USA.

The term "biocompatible plasticizer" refers to any material which is soluble or dispersible in the cyanoacrylate ester composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127[7] and 4,444,933[8] the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and acetyl tri-n-butyl citrate.

The term "polymerization inhibitor" refers to conventional inhibitors of cyanoacrylate esters including materials such as sulfur dioxide, glacial acetic acid, and the like. The polymerization inhibitor is typically employed in amounts effective to inhibit polymerization until application onto the mammalian skin. Because of its compatibility with topical skin applications, the polymerization inhibitor is preferably sulfur dioxide which is preferably employed at from about 50 to 500 ppm, preferably 200 to 500 ppm, based on the total weight of the composition. Other preferred polymerization inhibitors include glacial acetic acid, free radical inhibitors (e.g., hydroquinones, 4-methoxyphenol) and the like which can be used alone or in combination with $SO_2$.

The term "antimicrobial agent" refers to agents which destroy microbes (i.e., bacteria, fungi, viruses and microbial spores) thereby preventing their development and pathogenic action.

The term "antimicrobial cyanoacrylate ester composition" refers to polymerizable compositions comprising monomers and/or reactive oligomers of a cyanoacrylate ester or mixture of such esters and an antimicrobial agent. In a preferred embodiment the antimicrobial cyanoacrylate ester composition further comprises a biocompatible plasticizer and/or a polymerization inhibitor.

Compositions

This invention relates to methods for treating and/or protecting non-suturable superficial wounds with antimicrobial cyanoacrylate ester compositions which compositions are described in detail below.

As above, the compositions of this invention comprise a polymerizable cyanoacrylate ester and iodine/polymer complexes. The iodine/polymer complexes are compatible with the cyanoacrylate ester as assessed by the fact that these complexes are dispersible in the cyanoacrylate ester composition in antimicrobially effective concentrations and when so employed, do not cause premature polymerization of the cyanoacrylate ester and do not prevent effective polymerization of the cyanoacrylate ester when applied to mammalian skin. Moreover, the polymerizable cyanoacrylate ester compositions comprising such complexes form a flexible, durable polymeric film having the complex incorporated therein such that iodine is released from the film in sufficient amounts to provide an antimicrobial property to the film when formed in situ on mammalian skin.

As shown in the examples below, many other conventional antimicrobial agents, when added to the cyanoacrylate ester composition cause polymerization of the cyanoacrylate ester as evidenced by gel formation within 24 hours of such addition or, in the case of elemental iodine, prevent in situ polymerization of the cyanoacrylate ester on mammalian skin. Accordingly, such agents are not compatible with the cyanoacrylate ester compositions.

Antimicrobial cyanoacrylate ester compositions useful in the methods described herein are described by Greff, et al.,  in allowed U.S. patent application Ser. No. 08/781,409 filed Jan. 10, 1997 which application is incorporated herein by reference.

The compositions of this invention are prepared by adding the iodine/polymer complex to the cyanoacrylate ester composition. The iodine/polymer complex is preferably added as the commercially available solid composition rather than as the commercially available aqueous or ethanolic solution insofar as the solution can cause premature polymerization of the cyanoacrylate ester which is apparently due to solvent effects. Accordingly, the compositions described herein are preferably free of added solvents (e.g., water, organic solvents such as chloroform, methanol, ethanol, toluene, ethyl acetate, hexane, etc.).

Upon addition of the solid iodine/polymer complex to the cyanoacrylate ester composition, the resulting system is thoroughly mixed to obtain a homogeneous suspension.

The amount of iodine/polymer complex added to the cyanoacrylate ester composition is a sufficient amount such that the resulting polymeric film is antimicrobial. Preferably, from about 5 to about 40 weight percent of the iodine/polymer complex and more preferably from about 10 to 25 weight percent is added to the cyanoacrylate ester composition based on the total weight of the composition.

The specific amount of iodine/polymer complex required to effect antimicrobial properties in the resulting polymeric film can be readily measured by conventional in vitro assays measuring zones of microbial growth inhibition around the film. Zones of inhibition of at least 1 millimeter and preferably 3 millimeters from the edge of the film when tested in the manner of Example 2 below evidence that the polymeric film is antimicrobial. Assessing the amount of iodine/polymer complex required in the polymeric film to effect such a zone of inhibition is well within the skill of the art.

The composition of the antimicrobial complex and the cyanoacrylate ester can be formulated to a specific viscosity to meet disparate demands for the intended application of the composition. For example, relatively low viscosities are often preferred where application is to be made to a large surface area. This preference results from the fact that these forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. For low viscosity applications, viscosity ranges of from about 2 to 1,500 centipoise at 20° C. are preferred. More preferably, the cyanoacrylate ester employed in the composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000. Suitable thickening agents for the cyanoacrylate ester compositions described herein also include a polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate ester composition preferably includes a biocompatible plasticizer and such plasticizers are preferably included from about 10 to 30 weight percent and more preferably from about 18 to 25 weight percent based on the weight of the composition absent the antimicrobial agent. Particularly preferred biocompatible plasticizers for use in the compositions described herein are dioctylphthalate and tri-n-butyl acetyl citrate.

Additionally, the cyanoacrylate ester compositions described herein preferably include a polymerization inhibitor in an effective amount to inhibit premature polymerization of the composition. In a particularly preferred embodiment, this inhibitor is sulfur dioxide which is employed at from about 50 to 500 ppm based on the total weight of the composition absent the antimicrobial agent. Another preferred inhibitor is 4-methoxyphenol which is employed in an amount effective to inhibit premature polymerization, preferably at from about 100–500 ppm based on the total weight of the composition absent the antimicrobial agent. Still another preferred inhibitor is a mixture of glacial acetic acid and sulfur dioxide which is preferably employed at from about 50 to 500 ppm of sulfur dioxide based on the weight of the composition and from about 50 to 500 ppm of glacial acetic acid based on the weight of the composition each in the absence of the antimicrobial agent.

The cyanoacrylate ester compositions may additionally contain one or more optional additives such as colorants, perfumes, rubber modifiers, modifying agents, etc. In practice, each of these optional additives should be both miscible and compatible with the cyanoacrylate ester composition and the resulting polymer. Compatible additives are those that do not prevent the use of the cyanoacrylate esters in the manner described herein.

In general, colorants are added so that the polymer layer formed on the skin will contain a discrete and discernable color. Perfumes are added to provide a pleasant smell to the composition. Rubber modifiers are added to further enhance the flexibility of the resulting polymer layer. The amount of each of these optional additives employed in the composition is an amount necessary to achieve the desired effect.

Additionally, the cyanoacrylate ester composition can optionally comprise a formaldehyde scavenger compound such as those described by Leung, et al.[9] The use of such scavengers has been suggested as enhancing internal in vivo applications of cyanoacrylate esters.

Still further, it is contemplated that the cyanoacrylate composition can optionally comprise an acrylic monomer that will act as a polymeric plasticizer when it copolymerizes with the cyanoacrylate ester composition.[10]

Methods

In the methods of this invention, the above-described compositions are applied to non-suturable superficial or small wounds on the skin surface of a mammalian patient (e.g., human patient) under conditions wherein the cyanoacrylate ester polymerizes to form an antimicrobial film over such wounds. In general, the wound is usually first cleaned (soap/water and optionally a disinfectant) and dried and then sufficient amounts of cyanoacrylate ester composition are employed to cover or encase the wound and is preferably extended by at least about 1 centimeter beyond the wound.

For cuts, a sufficient amount of the antimicrobial cyanoacrylate ester composition is applied to join the opposing skin edges, and preferably the amount applied also encases the entire cut area. For scrapes, a sufficient amount is applied to encase the entire scrape area. In view of the antimicrobial nature of the resulting film, the methods of this invention are readily practiced in sterile and non-sterile environments.

Upon contact with skin moisture and tissue protein, the antimicrobial cyanoacrylate ester composition will polymerize or, in the case of compositions utilizing partially polymerized cyanoacrylate esters, will further polymerize, at ambient conditions (skin temperature) over about 10 seconds to 60 seconds to provide a solid polymeric film which forms over and strongly adheres to the surface of the skin, thus providing a protective layer to the wound area.

The antimicrobial cyanoacrylate ester composition is applied to provide an effectively thick film over the surface of the non-suturable superficial wound. Because the to-be-treated wound is superficial and does not extend beyond the dermal layer, any polymeric residues diffusing into or forming in the wound will be naturally extruded from the skin. Generally, the composition provides an antimicrobial polymeric film or coating over the wound area which when set is satisfactorily flexible and adherent to the tissue without premature peeling or cracking. Preferably, the resulting polymeric film has a thickness of less than about 0.5 millimeter (mm), and more preferably the film has a thickness of less than about 0.3 mm. In a particularly preferred embodiment, the thickness of the polymeric film is from about 0.05 millimeter to about 0.5 millimeter and even more preferably from about 0.05 millimeter to about 0.3 millimeter.

Polymeric films of such thicknesses form a physical barrier film over these non-suturable superficial wounds which film provides protection for the wound by providing an airtight, waterproof seal around and over the wound. Once applied, the film prevents bacterial and contaminant entry into the wound while simultaneously providing an antimicrobial environment under the film. Generally, the polymeric film does not limit dexterity but rather can promote faster wound healing.

In either case, the antimicrobial polymeric film should preferably be maintained in a unbroken manner over the entire wound area. This can be assured by careful application of the antimicrobial cyanoacrylate ester composition onto the skin/wound. Additionally, the use of a plasticizer will facilitate the maintenance of the polymeric film in an unbroken manner. However, in a preferred embodiment, to further ensure that the polymeric film is maintained unbroken, after the initial layer of composition has cured to provide for a polymeric film, a second, preferably thinner, layer can be applied over the polymeric film. Additional amounts of antimicrobial cyanoacrylate ester composition can be applied as needed to maintain an unbroken film over the wound area.

When the antimicrobial cyanoacrylate ester composition is applied to cover or encase the wound area, sufficient antimicrobial cyanoacrylate ester composition is preferably employed to form a film of less than about 0.5 mm thick and more preferably at least about 0.1 mm thick. Such films are formed by applying at least about 0.02 ml of antimicrobial cyanoacrylate ester composition per square centimeter of skin surface area, more preferably from about 0.02 to about 0.2 ml per square centimeter of skin and still more preferably from about 0.02 to about 0.05 ml of antimicrobial cyanoacrylate ester composition per square centimeter of skin.

The amount of antimicrobial cyanoacrylate ester composition applied onto the skin surface area can be controlled by the amount of composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the composition in a controlled dropwise manner. Other methods for the controlled dispersement of the antimicrobial cyanoacrylate ester composition are as described above including, by way of example, a conventional spray applicator, a brush or solid paddle applicator, and the like.

Upon application of the antimicrobial cyanoacrylate ester composition, the surface skin moisture, tissue protein, and temperature are sufficient to initiate polymerization of the composition upon application. Thereafter, the skin surface is maintained under suitable conditions to allow polymerization to proceed to formation of a polymeric film.

In general, the particular length of time required for polymerization will vary depending on factors such as the amount of composition applied, the temperature of the skin, the moisture content of the skin, the surface area of the wound, and the like. However, in a preferred embodiment, polymerization is generally complete within about 10 seconds to about 60 seconds while the skin is maintained at ambient conditions. During this period, the person to whom application of the antimicrobial cyanoacrylate ester composition has been made merely allows the composition to form a polymeric film while minimizing any action to prevent the composition from being dislodged from that portion of the skin where it was applied or to adhere to unintended objects. Excess polymer composition can be removed with acetone (nail polish remover). Removal can be readily conducted except in the case where the composition polymer binds to a sensitive skin part (e.g., eye lids) where it should be removed by a health care professional. After the antimicrobial cyanoacrylate film has formed, the coating strongly adheres to the skin, is flexible and waterproof, thereby protecting the wound area and promoting healing.

In general, the film will adhere to the skin for a period of about 1-4 days after which time it sloughs off. Additional applications can be made if desired.

The polymeric film protects non-suturable superficial wounds because the composition forms a polymeric film which extends over the entire surface of the wound to protect the wound in much the way a bandage does while, in the case of cuts, also joins together the separated skin surfaces. Because the film is waterproof, the patient is not prevented from bathing and other activities involving exposure to water during the period the polymeric film protects the wound.

The following examples illustrate certain embodiments of the invention but is not meant to limit the scope of the claims in any way.

EXAMPLES

In the examples below, all temperatures are in degrees celsius (unless otherwise indicated) and all percents are weight percent (also unless otherwise indicated) except for percent inhibition which is true mathematical percentage.

Additionally, the following abbreviations have the following meanings. If an abbreviation is not defined, it has its generally accepted meaning.

CFU= colony forming units
conc.= concentration
flex.= flexibility
dur.= durability
ml= milliliters
mm= millimeters
ppm= parts per million
PVP-$I_2$= polyvinylpyrrolidone iodine complex
SAB-DEX= Sabouraud Dextrose
TSA= trypticase soy agar

Example 1

The following example examines the compatibility of different antimicrobial agents in cyanoacrylate ester compositions. In particular, the composition employed monomeric n-butyl cyanoacrylate containing 100 ppm sulfur dioxide and 20 weight percent of dioctyl phthalate absent the antimicrobial agent. In each case, either 5 weight percent, 10 weight percent or 20 weight percent of the antimicrobial agent, based on the total weight of the composition, was added thereto and the properties of the resulting composition measured. The antimicrobial agents tested were elemental iodine, solid polyvinylpyrrolidone iodine, a 30% aqueous solution of polyvinylpyrrolidone iodine, silver nitrate, hexachlorophene, merbromin, tetracycline-HCl, tetracycline hydrate, and erythromycin (each of these antimicrobial agents were obtained from Aldrich Chemical Company, Milwaukee, Wisc., USA except for PVP-$I_2$ which was purchased from a commercial vendor).

The evaluation included assessing whether the antimicrobial agent was soluble or suspendable in the composition; whether the resulting composition cured upon contact with skin; whether curing provided for a polymeric film in situ on the skin; whether the polymeric film was flexible and durable. Solubility and suspendability were determined by visually. The ability of the resulting composition to cure in situ upon application to skin was measured by applying the cyanoacrylate ester composition onto the upper arm of a male human subject and determining whether polymerization proceeded (up to 5 minutes) and, if so, the time required for polymerization. Film forming capabilities on the skin were assessed by visual evaluation. Durability was assessed by determining whether the film was retained on the skin surface for at least 24 hours and flexibility was measured by the ability of the film to be retained on the skin without cracking or peeling for at least 24 hours. The results of this evaluation are summarized in Table I below:

TABLE I

| Antimicrobial Agent | Conc. | Soluble | Curable | Film Formed | Flex. | Dur. |
|---|---|---|---|---|---|---|
| elemental iodine ($I_2$) | ~20% | partially | No (when tested for 5 minutes) | — | — | — |
| PVP-$I_2$ solid | 10% | no suspension[2] | Yes (30 seconds) | Yes | Yes | Yes |
| PVP-$I_2$ solution | 10% | no, gelled[1] | — | — | — | — |

TABLE I-continued

| Antimicrobial Agent | Conc. Soluble | Curable | Film Formed | Flex. | Dur. |
|---|---|---|---|---|---|
| Silver nitrate | 5% no, gelled[1] | — | — | — | — |
| Hexachlorophene | 5% no, gelled[1] | — | — | — | — |
| Merbromin | 5% no, gelled[1] | — | — | — | — |
| tetracycline.HCl | 5% no, gelled[1] | — | — | — | — |
| tetracycline hydrate | 5% no, gelled[1] | — | — | — | — |
| Erythromycin | 5% no, gelled[1] | — | — | — | — |

[1] gel formation within 24 hours of addition of the antimicrobial agent evidences premature polymerization of the cyanoacrylate ester. In such cases, the antimicrobial agent initiates polymerization.

[2] the mixture is readily resuspended with mild agitation. No gel formed over an 8 week period when stored at room temperature.

The above data demonstrates that of the antimicrobial agents tested, only polyvinylpyrrolidone iodine complex was compatible with the cyanoacrylate ester composition and, of the polyvinylpyrrolidone iodine complexes tested, only the solid form was compatible. Evidently, the solvent in the solution form of polyvinylpyrrolidone iodine complex initiated polymerization of the cyanoacrylate ester. Significantly, the suspension formed by the addition of solid polyvinylpyrrolidone iodine complex was curable in situ on human skin resulting in a flexible and durable polymeric film.

In addition to the above, polyvinylpyrrolidone is a well known biocompatible polymer thereby evidencing that such polymers, when complexed with iodine, are suitable for use in the compositions described herein.

Example 2

The following example was conducted to determine whether sufficient polyvinylpyrrolidone iodine complex was incorporated into the polymeric cyanoacrylate film formed in situ to render this film antimicrobial.

A. Preparation of the Inoculum

Specifically, the surfaces of two TSA plates, 100×15 mm, were inoculated with stock cultures (maintained on TSA slants) with the following microorganisms using a sterile inoculating loop: Staphylococcus aureus (ATCC No. 6538) and Staphylococcus epidermidis (ATCC No. 12228). The plates were incubated at 30° to 35° C. for 24 hours. The surfaces of two SAB-DEX agar plates were streaked with Candida albicans and incubated at 20°–25° C. for 48 hours.

The cultures were harvested with sterile saline. Each culture suspension was collected in a sterile container and sufficient sterile saline was added to reduce the microbial count to obtain a working suspension of approximately $1 \times 10^8$ CFU's per ml.

The specific microorganisms recited above were selected for inclusion herein because they are common human skin pathogens (bacteria and fungus).

B. Inoculation of Plates

Each of the three test microorganisms was used to inoculate individual TSA plates by streaking them with sterile cotton tip applicators saturated with the appropriate suspension. The plates were allowed to dry.

C. Inhibition Study

Films of polymerized n-butyl cyanoacrylate comprising 0%, 10%, 15%, 20% or 30% iodine polyvinylpyrrolidone complex were formed on 25 mm glass fiber filter disks and then cut into approximately 11 to 13 mm pieces. The pieces were placed in the center of the appropriate inoculated TSA plates. An untreated filter disk was cut into half, and one-half was placed in the center of the appropriate inoculated TSA plate and the other one-half was place in the center of non-inoculated TSA plates, to serve as a negative control. Two inoculated plates of each microorganism were also used as positive controls without the test article. These plates were then incubated for 3 days at 30° to 35° C. After incubation, the plates were removed and examined for any signs of microbial growth inhibition.

The results of this analysis are set forth in Tables II–IV below. The sample sizes reported are the portion of the sample actually in contact with the agar. The sizes of the zone of inhibition include the diameters of the entire zone including the test article size.

TABLE II

Results for *Staphylococcus aureus*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12 | 15 |
| 15% PVP-$I_2$ | 12.5 | 14 |
| 20% PVP-$I_2$ | 11.5 | 15.5 |
| 30% PVP-$I_2$ | 12.5 | 20 |
| Untreated Filter Disk | 13[2] | 13[2] |
| Negative Control | 13[2] | 13[2] |
| Positive Control | n/a | 0 |

TABLE III

Results for *Staphylococcus epidermis*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 15 |
| 15% PVP-$I_2$ | 12 | 15.5 |
| 20% PVP-$I_2$ | 12.5 | 20.5 |
| 30% PVP-$I_2$ | 13 | 27.5 |
| Untreated Filter Disk | 13[2] | 13[2] |
| Negative Control | 13[2] | 13[2] |
| Positive Control | n/a | 0 |

TABLE IV

Results for *Candida albicans*

| SAMPLE: n-butyl cyanoacrylate comprising | SAMPLE SIZE[1] (in mm) | ZONE OF INHIBITION[1] (in mm) |
|---|---|---|
| 0% PVP-$I_2$ | 12 | 12 |
| 10% PVP-$I_2$ | 12.5 | 18.5 |
| 15% PVP-$I_2$ | 12.5 | 23 |
| 20% PVP-$I_2$ | 12.5 | 20.5 |
| 30% PVP-$I_2$ | 13 | 29.5 |
| Untreated Filter Disk | 13[2] | 13[2] |
| Negative Control | 13[2] | 13[2] |
| Positive Control | n/a | 0 |

[1] average of two runs
[2] single run only

The above data demonstrates that the compositions of this invention produce a polymeric cyanoacrylate film which have broad spectrum of antimicrobial activity. Based on these results, it is expected that these compositions would be antimicrobial when formed in situ on mammalian skin surfaces.

Example 3

An antimicrobial cyanoacrylate ester composition is prepared using n-butyl cyanoacrylate, 200 ppm sulfur dioxide, 200 ppm glacial acetic acid, 20 weight percent acetyl tri-n-butyl citrate and 15 weight percent of PVP-$I_2$ each based on the total weight of the composition. The composition is placed into a suitable dispensing device. Two drops of this composition are placed dropwise onto the skin of a knee having a superficial scrape of about 1 sq cm in size. After about 30 seconds, the cyanoacrylate ester will polymerize to form an antimicrobial film over the scrape.

From the foregoing description, various modifications and changes in the composition and method will occur to those skilled in the art. All such modifications coming within the scope of the appended claims are intended to be included therein.

What is claimed is:

1. A method for treating and/or protecting non-suturable superficial wounds which comprises:

applying to the surface of a non-suturable superficial wound a sufficient amount of an antimicrobial polymerizable cyanoacrylate ester composition so as to cover the entire wound area wherein the superficial wound is characterized as a superficial cut and/or an abrasion which does not penetrate through the dermal layer of the skin surface to the subcutaneous layer; and polymerizing the antimicrobial cyanoacrylate ester composition so as to join separated skin sections and/or to form an antimicrobial polymeric film which adheres to the area where the composition was applied, wherein the antimicrobial cyanoacrylate ester composition comprises:

(a) a polymerizable cyanoacrylate ester; and (b) an antimicrobially effective amount of a complex of iodine molecules with a biocompatible polymer.

2. A method according to claim 1 wherein the polymerizable cyanoacrylate ester is a polymerizable monomer or reactive oligomer of a cyanoacrylate ester which, in monomeric form, is represented by formula I:

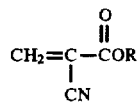

$$CH_2=C-COR \atop | \atop CN \qquad\qquad I$$

wherein R is selected from the group consisting of:
alkyl of 1 to 10 carbon atoms,
alkenyl of 2 to 10 carbon atoms,
cycloalkyl groups of from 5 to 8 carbon atoms, phenyl,
2-ethoxyethyl,
3-methoxybutyl, and a substituent of the formula:

$$\begin{array}{c} R' \quad O \\ | \quad\; \| \\ C- \;\; COR'' \\ | \\ R' \end{array}$$

wherein each R' is independently selected from the group consisting of:
hydrogen and methyl, and R'' is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

3. A method according to claim 2 wherein R is alkyl of from 4 to 10 carbon atoms.

4. A method according to claim 3 wherein R is selected from the group consisting of butyl, pentyl or octyl.

5. A method according to claim 4 wherein R is n-butyl.

6. A method according to claim 1 wherein said complex of iodine molecules with a biocompatible polymer is polyvinylpyrrolidone iodine.

7. A method according to claim 1 wherein the antimicrobial cyanoacrylate ester composition further comprises a biocompatible plasticizer.

8. A method according to claim 7 wherein said biocompatible plasticizer is dioctyl phthalate.

9. A method according to claim 1 wherein the antimicrobial cyanoacrylate ester composition further comprises a polymerization inhibitor.

10. A method for treating and/or protecting non-suturable superficial wounds which comprises:

applying to the surface of a non-suturable superficial wound a sufficient amount of an antimicrobial cyanoacrylate ester composition so as to cover the entire wound area wherein the wound is characterized as a superficial cut and/or an abrasion which do not penetrate through the dermal layer of the skin surface; and polymerizing the antimicrobial cyanoacrylate ester composition so as to join separated skin sections and/or to form an antimicrobial polymeric film which adheres to the area where the adhesive was applied, wherein the antimicrobial cyanoacrylate ester composition which comprises:

(a) a polymerizable cyanoacrylate ester which, in monomeric form, is represented by formula II:

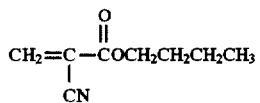

$$CH_2=C-COCH_2CH_2CH_2CH_3 \atop | \atop CN \qquad\qquad II$$

(b) an antimicrobially effective amount of polyvinylpyrrolidone iodine complex.

* * * * *